(12) United States Patent
Steinbaugh et al.

(10) Patent No.: US 9,623,223 B2
(45) Date of Patent: Apr. 18, 2017

(54) WOUND DRESSINGS COMPRISING A PLURALITY OF LIQUID-EXPANDABLE ARTICLES

(71) Applicant: RevMedx, Inc., Wilsonville, OR (US)

(72) Inventors: John Steinbaugh, Wilsonville, OR (US); Mary Bullard, Wilsonville, OR (US); Andrew Barofsky, Lake Oswego, OR (US)

(73) Assignee: REVMEDX, Inc., Wilsonville, OR (US)

( * ) Notice: Subject to any disclaimer, the term of this patent is extended or adjusted under 35 U.S.C. 154(b) by 34 days.

(21) Appl. No.: 14/163,962

(22) Filed: Jan. 24, 2014

(65) Prior Publication Data

US 2014/0142523 A1 May 22, 2014

Related U.S. Application Data

(63) Continuation-in-part of application No. 13/398,671, filed on Feb. 16, 2012.
(Continued)

(51) Int. Cl.
*A61F 13/00* (2006.01)
*A61L 15/28* (2006.01)
(Continued)

(52) U.S. Cl.
CPC ....... *A61M 35/00* (2013.01); *A61F 13/00008* (2013.01); *A61F 13/00051* (2013.01);
(Continued)

(58) Field of Classification Search
None
See application file for complete search history.

(56) References Cited

U.S. PATENT DOCUMENTS 1,785,831 A 12/1930 Edmundson
2,858,830 A 11/1958 Robins
(Continued)

FOREIGN PATENT DOCUMENTS

EP 2319471 A2 5/2011
WO 00/29484 5/2000
(Continued)

OTHER PUBLICATIONS

Krause, David, "Proposal to Reclassify the Absorbable Hemostatic Agent Device, Memo to General and Plastic Surgery Devices Panel Members," Food and Drug Administration, Jun. 4, 2002; pp. 1-8.
(Continued)

*Primary Examiner* — Kevin S Orwig
(74) *Attorney, Agent, or Firm* — Schwabe, Williamson & Wyatt, P.C.

(57) ABSTRACT

Provided herein are self-expanding wound dressings that include a first outer layer, a second outer layer, and a liquid-expandable layer disposed between the first outer layer and the second outer layer, wherein the liquid-expandable layer includes a plurality of liquid-expandable articles retained by a substrate, wherein the plurality of liquid-expandable articles expand to form expanded articles upon contact with a liquid. Also provided is a method of treating an individual having a bleeding wound, the method including applying a self-expanding wound dressing to the wound. Also provided are methods of manufacturing a wound dressing, the methods including forming an absorbent material into a plurality of liquid-expandable articles, coupling the plurality of liquid-expandable articles to a substrate to form a liquid-expandable layer, and positioning the liquid-expandable layer between a first outer layer and a second outer layer to form the wound dressing.

14 Claims, 8 Drawing Sheets

Related U.S. Application Data

(60) Provisional application No. 61/756,277, filed on Jan. 24, 2013, provisional application No. 61/443,520, filed on Feb. 16, 2011, provisional application No. 61/525,036, filed on Aug. 18, 2011.

(51) Int. Cl.

| | |
|---|---|
| *A61M 35/00* | (2006.01) |
| *A61F 13/02* | (2006.01) |
| *A61L 15/42* | (2006.01) |
| *A61L 15/60* | (2006.01) |

(52) U.S. Cl.
CPC ...... *A61F 13/0206* (2013.01); *A61F 13/0223* (2013.01); *A61F 13/0233* (2013.01); *A61F 13/0243* (2013.01); *A61L 15/28* (2013.01); *A61L 15/425* (2013.01); *A61L 15/60* (2013.01); *A61F 2013/00463* (2013.01); *A61F 2013/00468* (2013.01)

(56) References Cited

U.S. PATENT DOCUMENTS

| | | |
|---|---|---|
| 5,383,891 A | 1/1995 | Walker |
| 6,027,471 A | 2/2000 | Fallon et al. |
| 6,964,658 B2 | 11/2005 | Ashby et al. |
| 7,709,631 B2 | 5/2010 | Harris |
| 8,828,050 B2 | 9/2014 | Gregory |
| 2003/0095997 A1 | 5/2003 | Ruszczak et al. |
| 2003/0202970 A1 | 10/2003 | Liu et al. |
| 2004/0013715 A1 | 1/2004 | Wnek et al. |
| 2004/0122350 A1 | 6/2004 | Zhong et al. |
| 2006/0004408 A1 | 1/2006 | Morris et al. |
| 2006/0173492 A1 | 8/2006 | Akerfeldt et al. |
| 2006/0233869 A1 | 10/2006 | Looney et al. |
| 2007/0014862 A1 | 1/2007 | Pameijer et al. |
| 2007/0021703 A1 | 1/2007 | McCarthy |
| 2007/0100271 A1 | 5/2007 | Shimanuki |
| 2007/0148161 A1 | 6/2007 | Delmotte |
| 2007/0255238 A1 | 11/2007 | Cochrum et al. |
| 2008/0071207 A1 | 3/2008 | deLuis et al. |
| 2008/0171958 A1* | 7/2008 | Gundersen ......... A61F 13/0206 602/56 |
| 2009/0226391 A1 | 9/2009 | Roberts et al. |
| 2010/0129427 A1 | 5/2010 | Hen et al. |
| 2011/0077682 A1* | 3/2011 | Gregory ............ A61F 13/00008 606/213 |
| 2012/0209232 A1 | 8/2012 | Barofsky |

FOREIGN PATENT DOCUMENTS

| | | |
|---|---|---|
| WO | 02/22059 | 3/2002 |
| WO | 2010-129587 A1 | 11/2010 |
| WO | 2012/112797 A2 | 2/2013 |

OTHER PUBLICATIONS

Natuno, T., et al., "New Collagen Topical Hemostatic Agent-Comparative Evaluation in Experimental Animal Wounds," Jpn J Artif Organs, 1990, vol. 19, No. 3, pp. 1235-1238.

* cited by examiner

WOUND DRESSINGS COMPRISING A PLURALITY OF LIQUID-EXPANDABLE ARTICLES

CROSS REFERENCE TO RELATED APPLICATIONS

The present application is a Continuation-In Part of and claims priority to U.S. patent application Ser. No. 13/398,671, filed Feb. 16, 2012, entitled WOUND STASIS DRESSING FOR LARGE SURFACE WOUNDS, which in turn claims priority to U.S. Provisional Patent Application No. 61/525,036, filed Aug. 18, 2011 entitled "Wound Stasis Dressing for Large Surface Wounds," and to U.S. Provisional Patent Application No. 61/443,520, filed Feb. 16, 2011 entitled "Wound Stasis Dressing for Large Surface Wounds," the disclosures of which are hereby incorporated by reference in their entirety.

The present application also claims priority to U.S. Provisional Patent Application No. 61/756,277, filed Jan. 24, 2013, entitled SELF-EXPANDING WOUND DRESSINGS, the disclosure of which is also hereby incorporated by reference in its entirety.

GOVERNMENT INTERESTS

This invention was made with United States government support under Contract No. W911NF-11-C-0038. The Government has certain rights in the invention.

TECHNICAL FIELD

Embodiments herein relate to methods, compositions and devices for controlling bleeding and treating wounds.

BACKGROUND

Uncontrolled external hemorrhage is the leading cause of death on the battlefield and the second leading cause of death in civilian trauma. At the point of injury, every drop of blood is precious and cannot be replaced until the casualty reaches the next echelon of care. Wounds sustained from IED's, blasts, and small caliber missiles can cause open and penetrating wounds that are difficult to pack with KERLIX™ and hemostatic gauzes. Application of sufficient pressure on bleeding vessels to control hemorrhage is a constant challenge in austere environments. Further, treatment of a large wound can quickly deplete a medic's available supply of dressings.

Postpartum hemorrhage (PPH) is a leading cause of maternal mortality in low-income countries, and responsible for a quarter of all maternal deaths globally. The majority of all deaths related to PPH will occur within 24 hours following delivery and outside of a health care setting, where operative measures are not readily available. Nearly all of these deaths could be prevented by swift intervention with a series of non-operative and operative measures.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

Figure 1A:
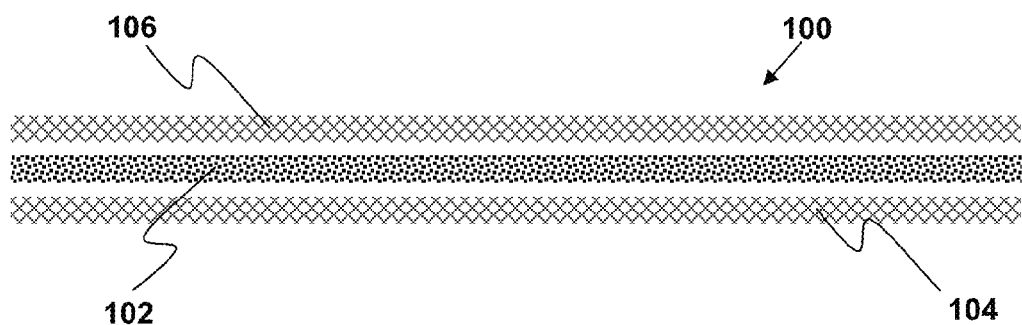
FIGS. 1A and 1B illustrate side views of two exemplary self-expanding wound dressing prior to expansion.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Embodiments herein provide self-expanding wound dressings comprising a liquid-expandable layer. In general, embodiments include methods for treating hemorrhagic injuries. More specifically, there is provided a method to effect rapid hemostatic response and control hemorrhage by introducing a self-expanding wound dressing into, on, or around a bleeding cavity. An embodiment also provides a method of preparing or manufacturing such a self-expanding wound dressing.

In the following description, unless further particularized or otherwise noted, the term "liquid-expandable" is intended to refer to any material or substance that expands in occupied volume upon contact with a liquid.

Embodiments provided herein are self-expanding wound dressings that include a plurality of layers, including a first outer layer, a second outer layer, and a liquid-expandable layer positioned between the first outer layer and the second outer layer. In various embodiments, the liquid-expandable layer may include a plurality of liquid-expandable articles that are retained by a substrate, such as a fibrous mesh or a backing layer. In various embodiments, the plurality of liquid-expandable articles expand to form expanded articles upon contact with a liquid. In various embodiments, the first outer layer, second outer layer, and a liquid-expandable layer are formed into elongated sheet.

In some embodiments, the self-expanding wound dressings disclosed herein may be in the form of an elongated sheet. For such embodiments, the sheet may be provided wrapped into a roll or z-folded such that a user may access a sufficient length of self-expanding wound dressing to cover wounds of varying sizes found on the patient's body. In such embodiments, the first outer layer, second outer layer, and a liquid-expandable layer may be laminated to form an elongated sheet. In other embodiments, the self-expanding wound dressings may have a peripheral boundary of predetermined size and shape sufficient to cover an afflicted wound area.

Also provided is a method of treating an individual having a bleeding wound, the method including applying a self-expanding wound dressing as disclosed herein to the wound. Additional embodiments are methods of manufacturing a wound dressing, the methods including forming an absorbent material into a plurality of liquid-expandable articles, coupling the plurality of liquid-expandable articles to a substrate to form a liquid-expandable layer, and positioning the liquid-expandable layer between a first outer layer and a second outer layer to form the wound dressing.

Figure 1B:
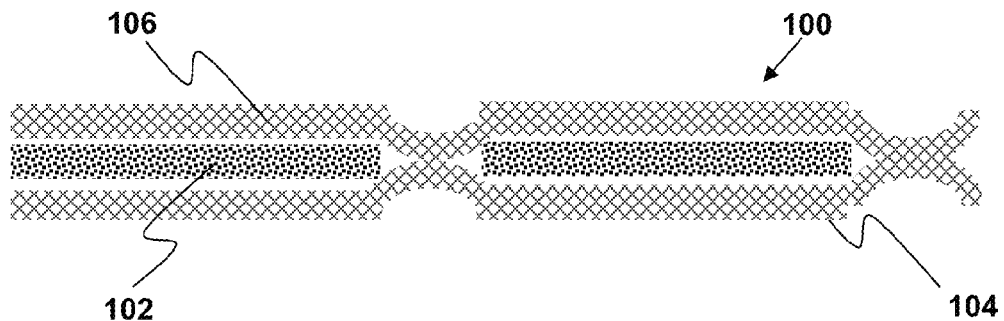
Figure 1C:
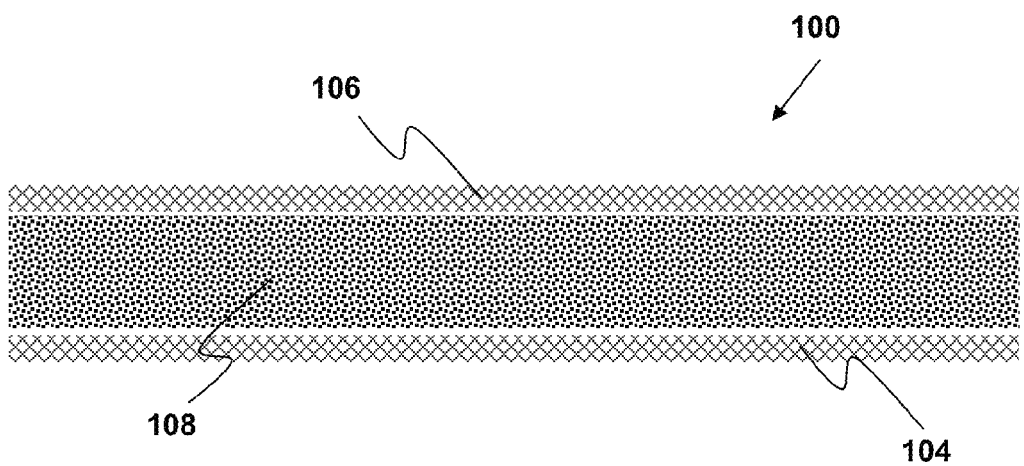
FIG. 1C depicts the self-expanding wound dressing of FIG. 1A following expansion of the liquid expandable layer, in accordance with various embodiments.

FIGS. 1A and 1B illustrate side views of two exemplary self-expanding wound dressing prior to expansion, and FIG. 1C depicts the self-expanding wound dressing of FIG. 1A following expansion of the liquid expandable layer, in accordance with various embodiments. As shown in FIGS. 1A and 1B, self-expanding wound dressing 100 includes a liquid-expandable layer 102 positioned between a first outer layer 104 and a second outer layer 106. In some embodiments, first outer layer 104 and second outer layer 106 may be joined at their peripheries to form one or more cells or pockets to receive liquid-expandable layer 102 therein. In particular embodiments, these cells or pockets may form a pattern or array. In such embodiments, first outer layer 104 and second outer layer 106 may be joined at additional points or lines internal their periphery, as illustrated in FIG. 1B. In some embodiments, the cells or pockets may be formed by welding together the two outer layers. In other embodiments, the cells or pockets may be formed by stitching together the two outer layers. In other embodiments, the cells or pockets may be formed by heat bonding together the two outer layers. In other embodiments, the cells or pockets may be formed by gluing together the two outer layers.

As illustrated in FIG. 1A, first outer layer 104 and/or second outer layer 106 may be flexible and porous. Exemplary porous materials for first outer layer 104 and second outer layer 106 may include fabrics, meshes and/or gauzes. For example, the first and second outer layers 104, 106 may be made of woven fabrics, nonwoven fabrics, melt-blown webs, foams, spun-bonded webs, thermal-bonded webs, spun-laced webs, paper, and/or thermally-embossed nonwoven fabrics. More precisely, specific, non-limiting examples of suitable first and second outer layers include woven fabrics, knitted fabrics, or non-woven fabrics of an organic polymer such as cotton, polyvinyl alcohol, or cellulose; paper; and perforated films of polyvinyl alcohol. In various embodiments, first and second outer layers 104, 106 may be elastic or non-elastic. In some embodiments, one of first outer layer 104 or second outer layer 106 may be non-porous.

In various embodiments, first outer layer 104 and second outer layer 106 may be made of the same material. In other embodiments, first outer layer 104 and second outer layer 106 may be made of different materials. For example, first outer layer 104 may be porous and second outer layer 106 may be non-porous. In various embodiments, first outer layer 104 may exhibit different fluid absorption properties than second outer layer 106.

FIG. 1C is a side view illustrating the expanded self-expanding wound dressing 100 of FIG. 1A following contact with a liquid. As shown in FIGS. 1A and 1C, liquid-expandable layer 102 (FIG. 1A) expands into an expanded layer 108 (FIG. 1C) upon contact with a liquid. In various embodiments, the liquid may be an aqueous solution, such as a bodily fluid. For example, in some embodiments, the liquid may be blood or serum. In various embodiments, once expanded, expanded layer 108 may be soft and pliable. Without being limited to any particular theory, this quality may permit self-expanding wound dressing 100 to conform to irregular wound crevices, gaps, and fissures.

In various embodiments, the expanded layer 108 occupies a volume greater than that of liquid-expandable layer 102. In various embodiments, the average volume ratio of the expanded layer to the liquid-expandable layer is at least 2× (in other words, the volume of the expanded layer is capable of expanding to at least 2 times the volume of the liquid-expandable layer). In other embodiments, the average volume ratio of the expanded layer to the liquid-expandable layer is at least 4×. In still other embodiments, the average volume ratio of the expanded layer to the liquid-expandable layer is at least 8×. In yet other embodiments, the average volume ratio of the expanded layer to the liquid-expandable layers is at least 10×.

In various embodiments, liquid-expandable layer 102 may be capable of expanding to 80% or greater of its maximum expansion capacity in 60 seconds or less following immersion in water or saline. In other embodiments, liquid-expandable layer 102 may be capable of expanding to 80% or greater of its maximum expansion capacity in 30 seconds or less following immersion in water or saline. In still other embodiments, liquid-expandable layer 102 may be capable of expanding to 80% or greater of its maximum expansion capacity in 10 seconds or less following immersion in water or saline. In yet other embodiments, liquid-expandable layer 102 may be capable of expanding to 80% or greater of its maximum expansion capacity in 5 seconds or less following immersion in water or saline. In certain environments, in use, liquid-expandable layer 102 may be unable to reach its maximum expansion capacity as it may be constrained in some manner, such as by the dimensions of the wound.

In various embodiments, the liquid expandable layer 102 may be uniformly distributed throughout self-expanding wound dressing 100. In other embodiments, the liquid expandable layer 102 may be asymmetrically distributed throughout self-expanding wound dressing 100. In this way, segments of self-expanding wound dressing 100 may exhibit an ability to self expand upon contact with a liquid, while other segments of the dressing may not.

In various embodiments, liquid-expandable layer 102 may include an absorbent material including, but not limited to, a sponge or fibrous material. In various embodiments, the absorbent material may include a polysaccharide such as, but not limited to, cellulose, starch, chitin, or chitosan. In some embodiments, liquid expandable layer 102 may include regenerated cellulose sponge. In other embodiments, the absorbent material may include synthetic sponges such as, but not limited to, various polyvinyl alcohol (PVA) polymers and derivatives thereof having desirable physical and mechanical properties. In various embodiments, liquid expandable layer 102 may be biodegradable and/or bioabsorbable.

In various embodiments, the absorbent material may form a contiguous sheet. In other embodiments, the absorbent material may include a plurality of distinct articles that move relatively independent of one another.

In various embodiments, liquid-expandable layer 102 may include a compressed material. As used herein, the term "compressed material" refers to a material that has a first size/dimension or form factor in an non-compressed state, and has a second, reduced size/dimension or form factor in a compressed state. In various embodiments, the compressed material may remain in essentially a compressed state indefinitely until hydrated. For these embodiments, and without being limited to any particular theory, the compressed material, when hydrated, may rapidly expand in an effort to assume its pre-compression dimensions. In this way, the compressed material may store additional mechanical energy in a compressed state, as compared to the non-compressed state, that is released when exposed to a liquid, thus causing liquid expandable layer 102 to quickly expand. In various embodiments, the absorbent material may be compressed by heat compression or any other suitable compression method known in the art.

In various embodiments, self-expanding wound dressing 100 may be sufficiently flexible to insert and pack into wounds. Accordingly, liquid expandable layer 102 may be adapted to be soft and flexible. In embodiments where the compressed material of liquid expandable layer 102 includes a contiguous sheet, the sheet may be mechanically softened to make it more flexible. In some embodiments, one or more regions of the sheet may be treated with repeated bending or flexing to reduce mechanical stiffness. In other embodiments, the sheet may be subjected to creping or microcreping to impart stretchability and conformability to the layer. Additional methods may include, microcorrugation and embossing. In other embodiments, the sheet may be prefolded so that it flexes along predetermined folds placed according to the product application. Another treatment for providing flexibility to liquid expandable layer is to perforate the sheet with a series of perforations along certain lines or areas.

Yet another embodiment provides random or patterned holes into or through the sheet. Still another embodiment provides for the sheet to be incised so that it flexes along the incision or incisions with the incision having a predetermined depth, pattern and location. In various embodiments, excising or notching the sheet may allow flexibility along the excisions or removed material areas. The sheet also may be fabricated with various thicknesses, such as waffling, with alternate lines of thick and thin portions.

Figure 2A:
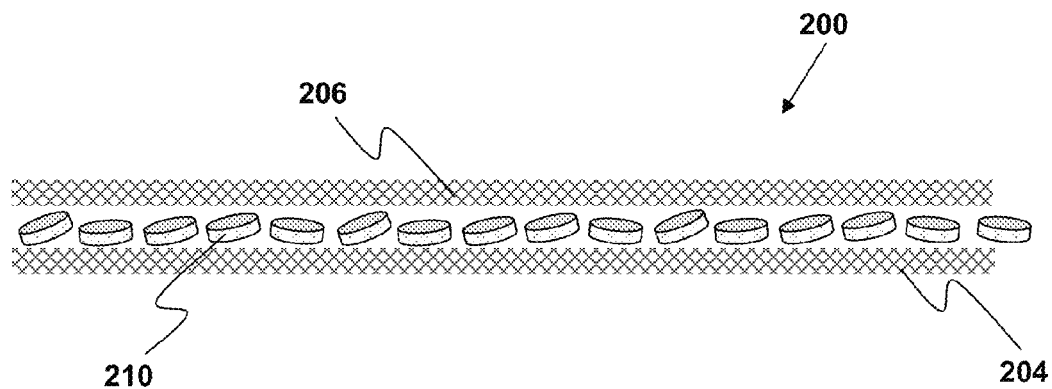
FIGS. 2A and 2B illustrate side views of another example of a self-expanding wound dressing wherein the liquid expandable layer includes a plurality of liquid-expandable articles, shown prior to expansion (FIG. 2A), and following expansion (FIG. 2B) of the liquid-expandable articles, in accordance with various embodiments.
Figure 2B:
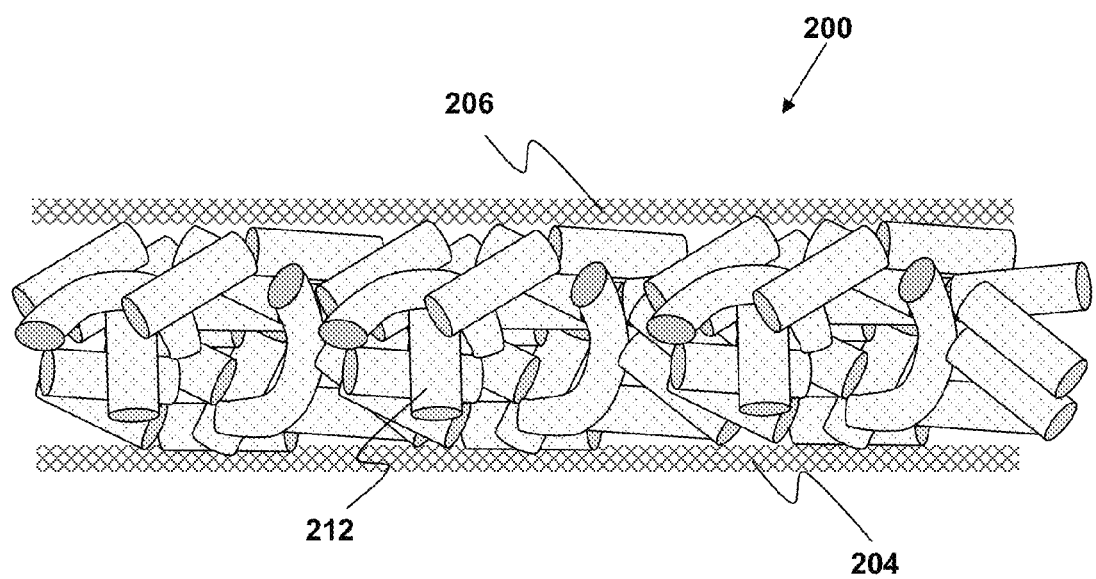

FIG. 2A is a side view of another embodiment of a self-expanding wound dressing 200, wherein liquid expandable layer 202 includes a plurality of liquid-expandable articles 210 that move independently of one another, thus creating a more flexible layer. FIG. 2B illustrates the expansion of liquid-expandable articles 210 following contact with a liquid. In various embodiments, the liquid-expandable articles may include one or more absorbent materials, which may be compressed materials in certain embodiments. In some embodiments, liquid-expandable articles 210 may include regenerated cellulose sponge. As shown in FIG. 2B, liquid-expandable articles 210 are adapted to expand into expanded articles 212 upon contact with a liquid. In various embodiments, the expanded articles 212 may have a volume greater than the liquid-expandable articles 210. As described above with respect to FIGS. 1A and 1B, in various embodiments, the average volume ratio of expanded articles to liquid-expandable articles may be between about 2× and about 12×, or even more. Additionally, in various embodiments, liquid-expandable articles 210 may be capable of expanding to 80% or greater of their maximum expansion capacity in 60 seconds or less following immersion in water or saline, such as about 30 second, about 10 seconds, about 5 seconds, or even less.

In various embodiments, self-expanding wound dressing 200 may include at least 3 liquid-expandable articles 210, such as about 10, 50, 100, or even more liquid-expandable articles. In various embodiments, the occupied volume of each liquid-expandable article 210 prior to expansion may be from 0.7 mm$^3$ to 7000 mm$^3$, such as from about 500 mm$^3$ to 5000 mm$^3$. In some embodiments, the volume of each liquid-expandable article may be greater than 1 mm$^3$ prior to expansion, such as about 5 mm$^3$, about 10 mm$^3$, about 50 mm$^3$, or about 100 mm$^3$, or even greater. In various embodiments, liquid-expandable articles 210 may all be uniform in size or may include a mixture of sizes.

In various embodiments, liquid-expandable articles 210 may have one or more predetermined shapes, based on adjustments to the length, width, diameter, or cross-sectional shape. Without being limited by theory, the shape, size and/or pattern of liquid-expandable articles 210 may influence the pliability of self-expanding wound dressing 200, as well as the ability of the self-expanding wound dressing to fit into, expand, fill, partially fill and conform to a wound cavity. In addition, the shape may assist expanded articles in retaining a desired position in the wound cavity. In FIGS. 2A and 2B, liquid-expandable articles 210 are depicted as a cylindrical shape. This notwithstanding, the predetermined shape of liquid-expandable articles 210 may include other articles with round, triangular, square, rectangular, hexagonal, conical, or octagonal cross-sections. In various embodiments, predetermined shapes having multiple projections (e.g., a star) may be used. In other embodiments, self-expanding wound dressing 200 may include liquid-expandable articles 210 with haphazard, random, irregular, or jagged shapes. In various embodiments, self-expanding wound dressing 200 may include liquid-expandable articles 210 of two or more predetermined shapes. In other embodiments, self-expanding wound dressing 200 may include liquid-expandable articles 210 that have a mixture of predetermined shapes and/or irregular shapes.

In various embodiments, the predetermined shape of liquid-expandable articles 210 may define any shape having first major outer surface and a second major outer surface. For such embodiments, the first major outer surface and the second major outer surface may be substantially parallel to one another. In various embodiments, the average distance between the outer surfaces may be from 0.5 mm to 20 mm, such from 1 mm to 10 mm, or from 1 mm to 5 mm. In various embodiments, such as the illustrated embodiment, liquid-expandable articles 210 may be substantially in the form of a disk or cylinder. For such embodiments, the average diameter of the first major outer surface and the second major outer surface may be from 1 mm to 20 mm, such from 5 mm to 10 mm. In various embodiments, self-expanding wound dressing 200 may include liquid-expandable articles 210 having the same average diameter or a mixture of liquid-expandable articles 210 having different average diameters.

Figure 3A:
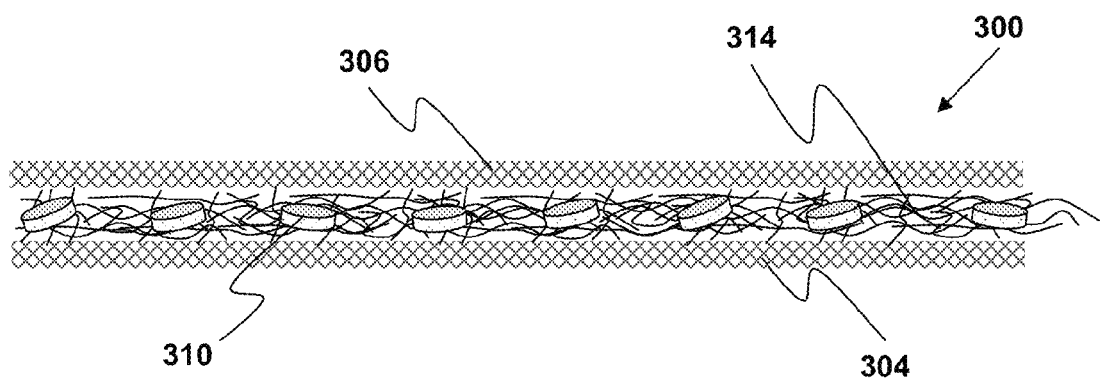
FIGS. 3A and 3B illustrate side views of another example of a self-expanding wound dressing wherein the liquid expandable layer includes a plurality of liquid-expandable articles that are retained by a web material, shown prior to expansion (FIG. 3A), and following expansion (FIG. 3B) of the liquid-expandable articles, in accordance with various embodiments.
Figure 3B:
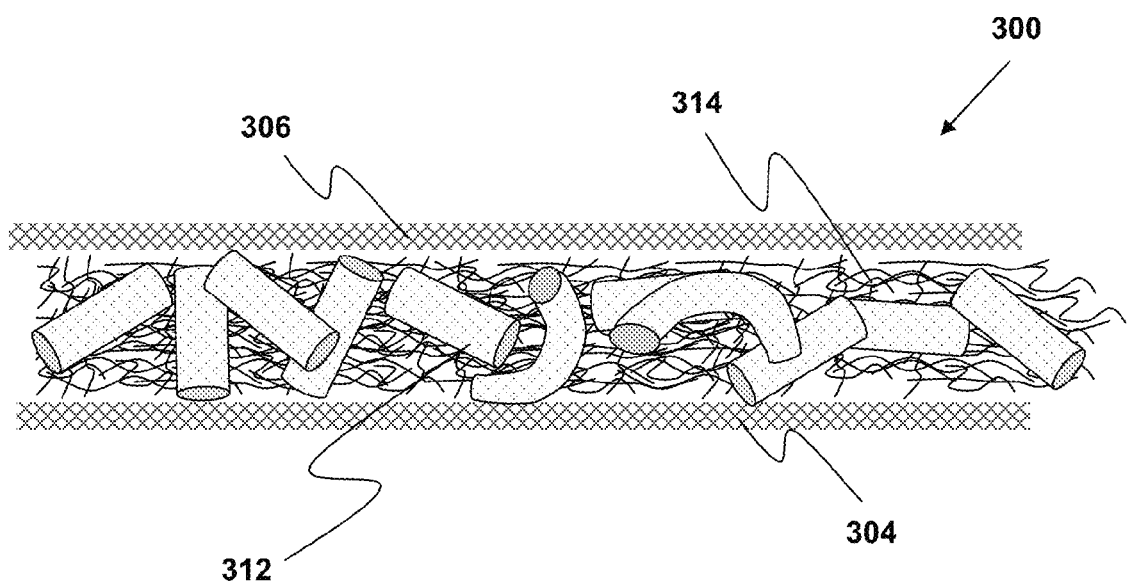

In various embodiments, the liquid-expandable articles may be retained by a substrate to restrict the liquid-expandable articles from moving freely throughout the space between the outer layers. In such embodiments, the liquid expandable layer may include a substrate such as a fibrous web, mesh, fabric, or other material intended to limit movement of the liquid-expandable articles. FIGS. 3A and 3B illustrate side views of another example of a self-expanding wound dressing wherein the liquid expandable layer includes a plurality of liquid-expandable articles that are spatially constrained by a web material, shown prior to expansion (FIG. 3A), and following expansion (FIG. 3B), in accordance with various embodiments. As can be seen in FIG. 3A, layer 302 includes a web material 314. In various embodiments, liquid-expandable articles 310 may be physically trapped, spatially constrained, or immobilized by web material 314. In some embodiments, the outer surfaces of the liquid-expandable articles 310 may be barbed, or roughened, so that the liquid-expandable articles 310 will catch on some of the fibers in web material 314, affording a degree of mechanical bonding to web material 314. In some embodiments, the mechanical bonding may be sufficient to prevent the liquid-expandable articles 310 from moving freely throughout the space between the outer layers, but not so great that the flexibility of the self-expanding wound dressing 300 is detrimentally affected. In various embodiments, woven or non-woven textile structures may be used for web material 312. Exemplary materials may include meshes, gauzes, fabrics, nonwoven fabrics, melt-blown webs, spun-bonded webs, thermal-bonded webs, spun-laced webs and/or undercast padding. In some embodiments, web material 314 may be treated to increase friction and entrapment of liquid-expandable articles, such as with a slip resistant coating or surface roughening.

FIG. 3B illustrates the self-expanding wound dressing 300 following expansion of the liquid-expandable articles 310 immobilized by web material 314, such as following contact with a liquid. In various embodiments, the degree of mechanical bonding to web material 314 should not be so great that the ability of liquid-expandable articles 310 to expand into expanded articles 312 is detrimentally affected.

Figure 4A:
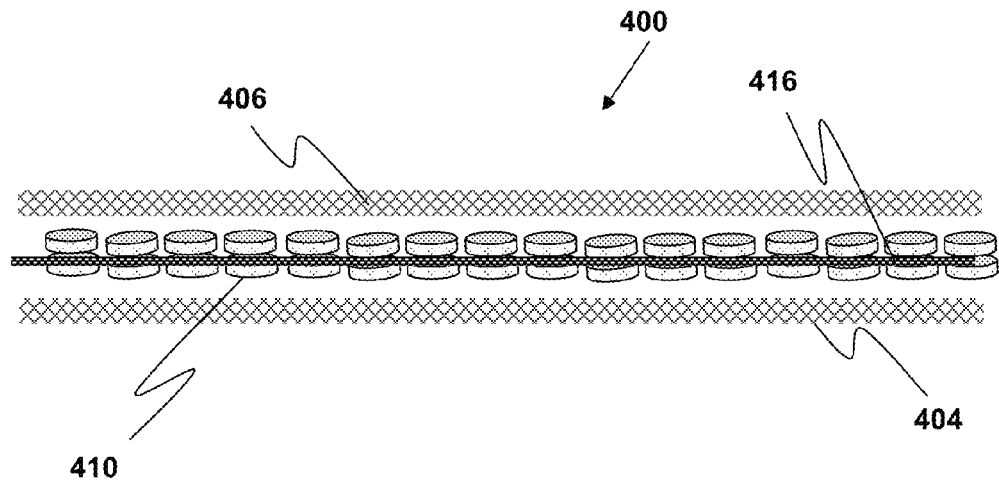
FIGS. 4A and 4B illustrate side views of another example of a self-expanding wound dressing wherein the liquid expandable layer includes a plurality of liquid-expandable articles that are connected to a backing layer, shown prior to expansion (FIG. 4A), and following expansion (FIG. 4B) of the liquid-expandable articles, in accordance with various embodiments.
Figure 4B:
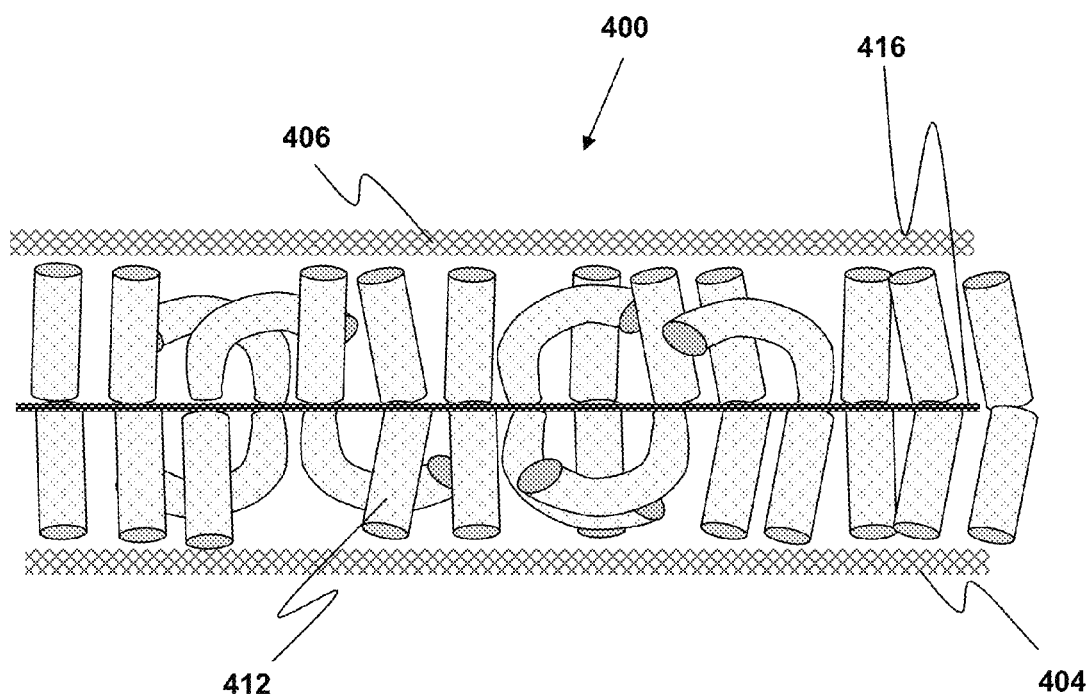

In various other embodiments, the liquid-expandable articles may be connected to a substrate to limit their movement. In such embodiments, the substrate may comprise a backing layer or sheet. FIGS. 4A and 4B illustrate side views of another example of a self-expanding wound dressing 400 wherein the liquid expandable layer includes a plurality of liquid-expandable articles that are connected to a backing layer, shown prior to expansion (FIG. 4A), and following expansion (FIG. 4B) of the liquid-expandable articles, in accordance with various embodiments. In various embodiments, liquid-expandable articles 410 may be arranged on a backing layer 416 in a predetermined pattern or array. As used herein, the term "predetermined pattern" refers to a designed arrangement. In various embodiments, the designed arrangement is formed by selecting positioning and/or orientation of the liquid-expandable articles. The term "predetermined pattern" includes any intentionally formed pattern and does not include a heterogeneously random arrangement, an inconsistently formed arrangement, or an unpredictable arrangement.

In various embodiments, the liquid-expandable articles may form a 3-dimensional array on top of backing material 416. The attachment points of the liquid-expandable articles may, in an embodiment, be substantially coplanar with each other. In some embodiments, liquid-expandable articles 410 may be disposed on one side of the backing layer 410, whereas in other embodiments, liquid-expandable articles 410 may be disposed on both sides of backing layer 416.

FIGS. 5A-5D are top views illustrating four different embodiments of self-expanding wound dressings wherein liquid-expandable articles are arranged on a backing layer in a predetermined pattern, in accordance with various embodiments. As illustrated, a plurality of liquid-expandable articles 510a, 510b, 510c, 510d may be arranged on a backing layer 516a, 516b, 516c, 516d in a predetermined pattern. In some embodiments, the liquid-expandable articles in the predetermined pattern are spaced sufficiently far apart so that the self-expanding wound dressing remains flexible.

Figure 5A:
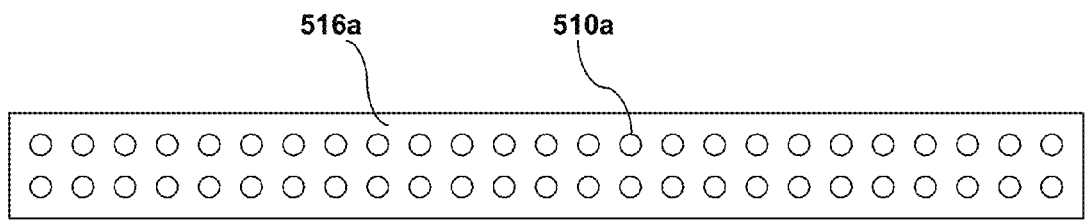
FIGS. 5A-5D are top views illustrating four different embodiments of self-expanding wound dressings wherein liquid-expandable articles are arranged on a backing layer in a predetermined pattern, in accordance with various embodiments.
Figure 5B:
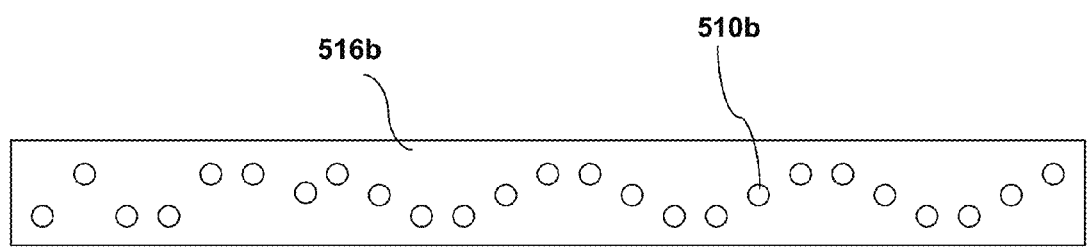
Figure 5C:
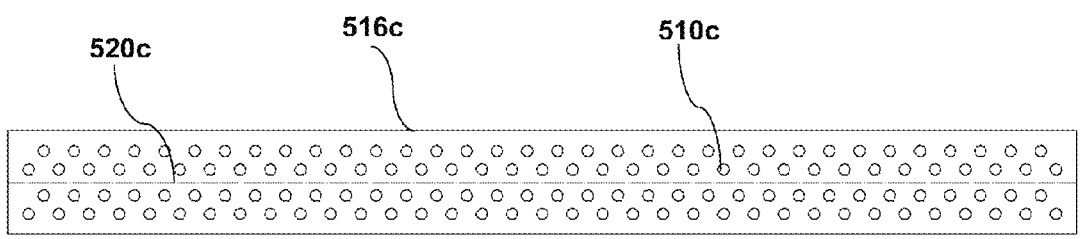
Figure 5D:
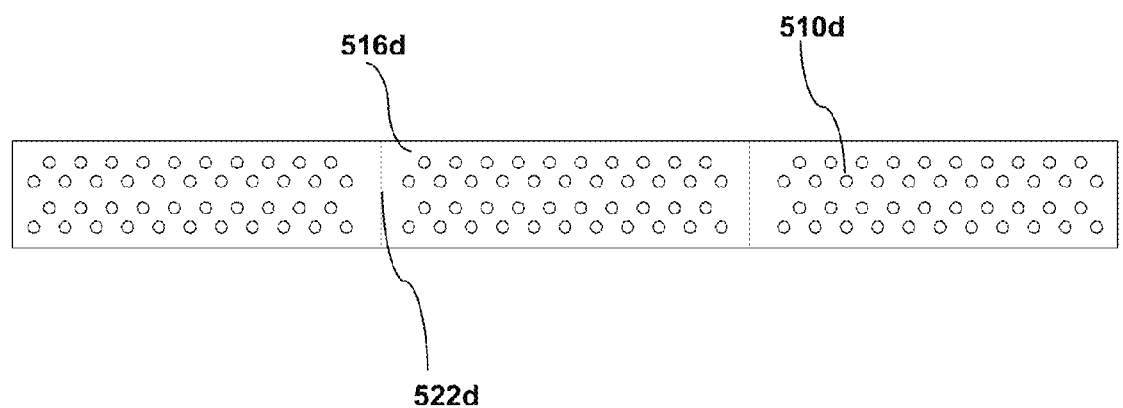

In various embodiments, the predetermined pattern may define one or more regions without any liquid-expandable articles. Theses article-free regions may be used as fold lines that allow the self-expanding wound dressing to be folded at a particular location on the dressing. As shown in FIG. 5C, some embodiments may include one or more fold lines 520c, which may increase the flexibility of the self-expanding wound dressing, or which may help the self-expanding wound dressing conform to a particular would size or shape or fit into a desired packaging. In additional embodiments, as shown in FIG. 5D, one or more article-free regions may be used as cut lines 522d that function to identify where a user may cut the dressing without being impeded by liquid expandable articles.

In various embodiments, the predetermined pattern may include the plurality of the liquid-expandable articles 510 being arranged in a substantially parallel orientation. In one embodiment, the predetermined pattern may include the plurality of liquid-expandable articles 510 being arranged in substantially linear orientation. In other embodiments, the predetermined pattern may include the plurality of the liquid-expandable articles 510 being arranged in a curved orientation. In other embodiments, the predetermined pattern includes the plurality of the liquid-expandable articles being arranged in a staggered orientation. In one embodiment, the predetermined pattern is a complex predetermined pattern (for example, a non-linear pattern, a curved pattern, or a geometric pattern such as a square, a rectangle, a circle, an oval, or other suitable shape).

In some embodiments, the backing layer and the liquid-expandable articles may be constructed from different materials. In other embodiments, the backing layer and the liquid-expandable articles may be constructed from the same material.

In various embodiments, the backing layer may be a porous or non-porous material. Exemplary non-porous materials may include polyurethane, polyethylene, and/or silicone films or sheets. Exemplary porous materials may include fabrics, meshes and/or gauzes. For example, in some embodiments, a porous backing material may be made of fabrics, nonwoven fabrics, melt-blown webs, foams, spun-bonded webs, thermal-bonded webs, spun-laced webs, paper, and/or thermally-embossed nonwoven fabrics. More precisely, examples of the substrate may be woven fabrics; knitted fabrics; or non-woven fabrics of an organic polymer such as cotton, polyvinyl alcohol, or cellulose; paper; and perforated films of polyvinyl alcohol. In various embodiments, the backing layer may be elastic or non-elastic.

Figure 6A:
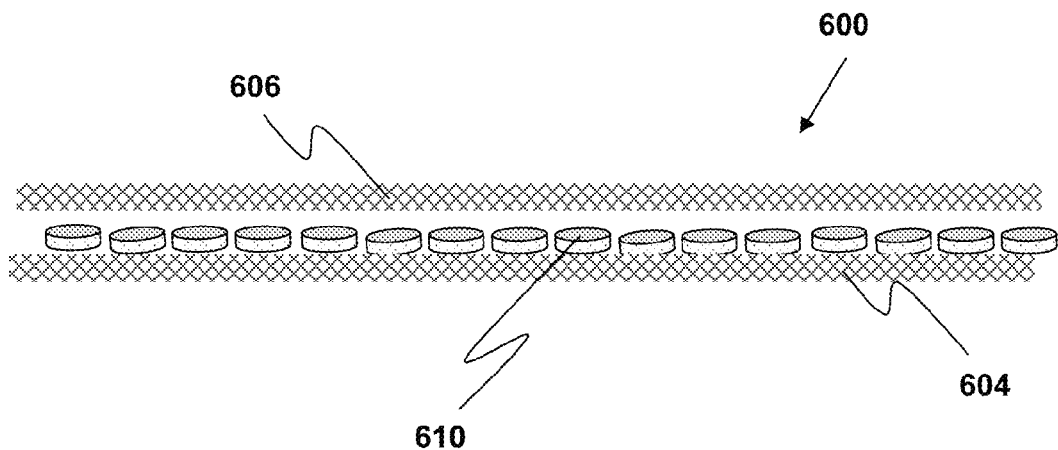
FIGS. 6A and 6B illustrate side views of another example of a self-expanding wound dressing wherein the liquid expandable layer includes a plurality of liquid-expandable articles that are connected to the first outer layer, shown prior to expansion (FIG. 6A), and following expansion (FIG. 6B) of the liquid-expandable articles, in accordance with various embodiments.
Figure 6B:
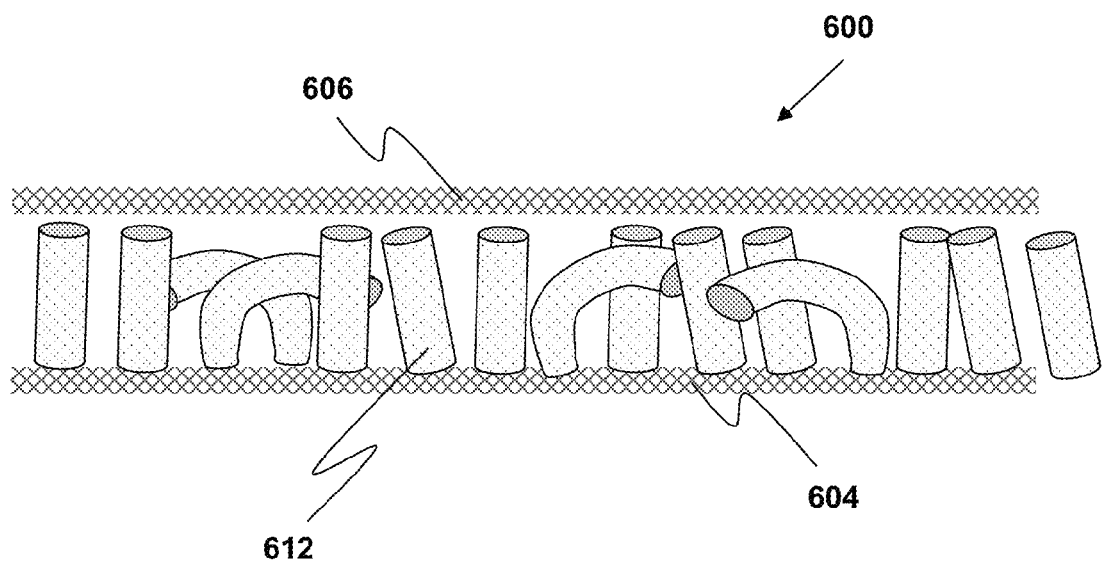

In various embodiments, instead of being connected to a backing layer, the liquid-expandable articles may be connected to one or both of the outer layers to limit movement of the liquid-expandable articles. FIGS. 6A and 6B illustrate side views of another example of a self-expanding wound dressing wherein the liquid expandable layer includes a plurality of liquid-expandable articles that are connected to the first outer layer, shown prior to expansion (FIG. 6A), and following expansion (FIG. 6B) of the liquid-expandable articles, in accordance with various embodiments. In the illustrated embodiment, liquid-expandable articles 610 are arranged on first outer layer 604 in a predetermined pattern, though in alternate embodiments, the liquid expandable articles 610 may be disposed on the second outer layer or both outer layers. In various embodiments, the liquid-expandable articles may form a 3-dimensional array on top of the outer layer.

In various embodiments, the liquid-expandable articles may be connected to the backing material or outer layers with an adhesive. Exemplary adhesives include cyanoacrylates, epoxies, light cure adhesives, silicones, urethanes hydro gels, acrylics, silicone gels, silicone PSA and hydrocolloids. In other embodiments, other mechanisms may be used to secure the liquid-expandable articles to the backing material or outer layers such as molding, stitching, etc. In some embodiments, the liquid-expandable articles may be heat bonded to the backing material or outer layers. In such embodiments, the liquid-expandable articles may be bonded to the backing material using a melted polypropylene layer.

In another embodiment, a unitary construct having a backing component and a plurality of liquid-expandable articles (protrusions) may be provided. In such an embodiment, the two components of the construct may be made of the same material, but are designed for different purposes. For example, the backing component may provide support for the liquid-expandable protrusions. However, because the backing component is made from the same material as the liquid-expandable protrusions, the backing component may also undergo expansion in response to liquid contact. In one embodiment, the backing component may be compressed to a lesser degree than the protrusions, such as providing a compression ratio of from 2:1 to 5:1 (protrusions:backing). In some embodiments, the backing may be formed in a relatively thin layer so as to provide support but retain flexibility. In specific embodiments, a suitable thickness of the backing (prior to liquid contact) may be approximately 1-5 mm, for example about 4 mm or about 2 mm. In various embodiments, the liquid-expandable protrusions may be configured to extend into various smaller areas of a wound. The liquid-expandable protrusions may be formed in any suitable number, and may have a variety of shapes and sizes as discussed elsewhere in this disclosure. In an embodiment, the construct may be formed by molding or etching, such as laser etching, a shaped element.

In various embodiments, self-expanding wound dressings described herein may further include one or more therapeutic agents. For example, in some embodiments, the self-expanding wound dressing may be impregnated, suffused, or coated with one or more therapeutic agents, and/or the one or more therapeutic agents may be dispersed throughout the self-expanding wound dressing. In some embodiments, the one or more therapeutic agents may be provided only on the liquid-expandable articles, only on an outer layer or layers, or a combination of both. In various embodiments, the one or more therapeutic agents may be selected from the group consisting of analgesics, steroids, antihistamines, anesthetics, bactericides, disinfectants, fungicides, vasoconstrictors, chemotherapeutic drugs, antibiotics, keratolytics, cauterizing agents, antiviral drugs, epidermal growth factor, fibroblast growth factors, transforming growth factors, glycoproteins, fibrinogen, fibrin, humectants, preservatives, lymphokines, cytokines, odor controlling materials, vitamins, and clotting factors.

In various embodiments, the one or more therapeutic agents may include hemostatic agent(s). For example, the one or more therapeutic agents may include chitosan or a derivative of chitosan. In other embodiments, the one or more therapeutic agents may include kaolin. In other embodiments, the one or more therapeutic agents may be selected from the group consisting of diatomaceous earth, silica, clays, minerals, attapulgite, bentonite, zeolite, and bioactive glasses.

In various embodiments, the one or more therapeutic agents may include an inorganic salt. Examples of an inorganic salt include, but are not limited to, a divalent ion selected from the group consisting of zinc, copper, magnesium, calcium and nickel, as well as $CaO$, $CaCl_2$, $AgNO_3$, $Ca(NO_3)_2$, $Mg(NO_3)_2$, $Zn(NO_3)_2$, $NH_4NO_3$, $AgCl$, $Ag_2O$, zinc acetate, magnesium acetate, calcium citrate, zinc citrate, magnesium citrate, magnesium chloride, magnesium bromide, zinc chloride, zinc bromide, calcium bromide, calcium acetate and calcium phosphate.

In various embodiments, the self-expanding wound dressing may include one or more markers for identifying the location of the dressing in a wound and/or facilitating removal of the dressing from the wound. In such embodiments, the marker may be coupled to the first and/or second outer layers. In other embodiments, the marker may be coupled to the liquid expandable articles. In some embodiments, the marker may include a radio-frequency identification (RFID) tag. In other embodiments, the marker may include a radiopaque material. For example, the marker may include a radiopaque filament, bead, ball, sphere, wire, or strip. In other examples, the marker may include a barium sulfate-infused polymer, such as polypropylene. In still other examples, at least a portion of the self-expanding wound dressing may be suffused with a radiopaque material. In yet another example, at least a portion of the self-expanding wound dressing may be coated with a radiopaque material.

Also provided herein are methods for effecting rapid hemostatic response and hemorrhage control by applying a self-expanding wound dressing to a bleeding wound. For example, a self-expanding wound dressing may be delivered into a wound cavity where the liquid-expandable layer may contact blood within the cavity and subsequently expand to form an expanded layer.

In various embodiments, applying a self-expanding wound dressing to a wound may include applying the self-expanding wound dressing by hand. In some embodiments, the self-expanding wound dressing may be applied to a wound using a securing adhesive. In another embodiment, the self-expanding wound dressing may be wrapped around a wound site, such as around an arm, leg, torso, etc.

In various embodiments, applying a self-expanding wound dressing to a wound may include applying the self-expanding wound dressing using an applicator. For example, the applicator may include a body, a tip, and a delivery mechanism. The body defines a storage chamber for the self-expanding wound dressing and has an opening for deploying the self-expanding wound dressing from the storage chamber. A tip may cover the opening and has a closed state wherein the tip maintains the self-expanding wound dressing in the storage chamber and an open state wherein the self-expanding wound dressing can be deployed through the opening and the tip.

Exemplary wounds often arise from, but are not limited to, traumatic accidents, projectiles from weapons, or improvised explosive devices which may create large soft tissue wounds in the calf, thigh, buttocks or shoulder that result in severe bleeding. Such wounds may be associated with an arterial puncture, a venous puncture, an arterial laceration and/or a venous laceration. Each wound can have a unique size and/or shape. Often, the extent of the tissue damage cannot be determined until emergent care can be provided. The use of the self-expanding wound dressings disclosed herein may allow for the treatment of several different wound types.

A method of preparing a self-expanding wound dressing in accordance with various embodiments is also provided. In some embodiments, a liquid-expandable material may be prepared by compressing an absorbent material to form a compressed absorbent material. This may be accomplished, for example, using conventional mechanical compression techniques well known to those skilled in the art. In other embodiments, compressing the absorbent material into a liquid-expandable material may include freeze-drying the absorbent material. Exemplary absorbent materials include sponges. In some embodiments, the liquid expandable layer may be adapted to be flexible in accordance with various methods described above.

In other embodiments, the liquid expandable layer may be adapted to be flexible by forming the compressed absorbent material into a plurality of liquid-expandable articles. This may include forming the compressed absorbent material into desirable shapes and sizes. For such embodiments, the liquid-expandable material may be cut using, for example, a die and press. The absorbent material may also be molded directly into desired shapes and sizes. In various embodiments, the absorbent material may be formed into a plurality of liquid-expandable articles by extrusion, pelletization, briquetting, tabletting, or other methods familiar to those skilled in the art. Alternatively, the absorbent material may be mechanically crushed into irregular shaped lumps, with desirable size ranges to be separated out by a classifier.

In various embodiments, the liquid-expandable articles may be arranged into a predetermined pattern and connected to a backing material or outer layer of the dressing. In other embodiments, the liquid-expandable articles may be co-formed, such as co-molded, with the backing material. In some embodiments, connecting liquid-expandable articles to a backing material may include using an adhesive. Exemplary adhesives include cyanoacrylates, epoxies, light cure adhesives, silicones, urethanes hydrogels, acrylics, silicone gels, silicone PSA, and hydrocolloids. In another embodiment, connecting liquid-expandable articles to a backing material may include heat bonding. For such embodiments, liquid expandable articles may be heat bonded using a heat sealable material such as polypropylene.

In various embodiments, the self-expanding wound dressing may be combined with one or more therapeutic agents by impregnating, suffusing, coating or dispersing the one or more therapeutic agents on or throughout the absorbent material. In an embodiment, the therapeutic agent may be sprayed onto the absorbent material. In another embodiment, the absorbent material may be soaked in a therapeutic agent solution.

Embodiments also provide a composition that includes a self-expanding wound dressing and a liquid expandable layer that is configured to induce hemostasis when contacted with blood and that may be applied to many types of wounds. In various embodiments, the liquid expandable layer may possess an ability, upon contact with blood, to rapidly expand to form a pliable, shapeable and conformable mass. Without limiting the scope of the disclosure, this mass may exert mechanical pressure on the surface of the wound, as well as interact with blood components to ultimately facilitate the formation of a fluid arresting coagulum within the wound cavity. In various embodiments, the combination of mechanical pressure and enhanced clotting may make the composition able to curtail bleeding without the application of external compression. In other embodiments, liquid-expandable layer may be capable of expanding through a swelling mechanism. While it is noted above that external compression is not necessary, in some embodiments, external compression may be used in conjunction with the self-expanding wound dressing. Such external compression may be provided by an elastic backing material or by a separate elastic or compression material/device.

Without limiting the scope of the disclosure, the devices and compositions disclosed herein may be advantageous for several reasons. In various embodiments, the liquid-expandable dressings disclosed herein have the ability to quickly expand into an expanded dressing. This allows the expanded dressing to quickly fill the wound cavity and provide a rapid hemostatic effect. Additional advantages include improved positioning within the wound, improved tissue apposition, and better conformation to intricate wound contours. The soft, pliable nature of the dressing, in connection with spring-like characteristics, permits the expanded dressing to provide a gentle outward pressure within the wound cavity, without the need to apply excessive pressure that can compromise perfusion to local tissues. Because the expanded articles conform to the wound cavity, pressure is exerted multi-directionally to address all bleeding points. The ability to exert outward pressure against and closely conforming to surrounding tissue surfaces helps the expanded dressing to maintain positioning within the wound cavity in the face of high flow arterial bleeding and deformation during transport of the injured person, maximize the contact and application of material at the sources of bleeding, and ensure constant and gentle, yet effective, compression within the wound cavity (without creating harmful pressure points).

EXAMPLES

Example 1

Figure 7:
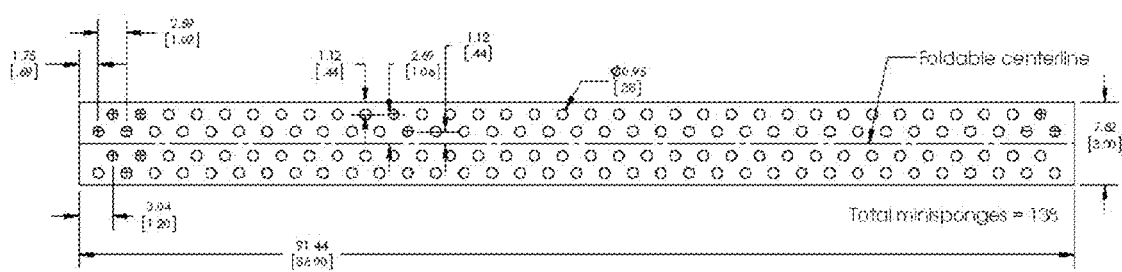

Preparation of a Self Expanding Wound Dressing With Compressed Cellulose Sponges This Example provides an exemplary method of making a self-expanding would dressing in accordance with various embodiments. A plurality of 40 mm thick regenerated cellulose sponge blocks were compressed to a compressed thickness of approximately 4 mm and die cut into 9.8 mm disks ("sponge disks"). A total of 138 sponge disks were arranged in a staggered pattern (end to end) on a 7.6 cm×91.4 cm viscose/polyester spunlace fabric (backing layer) as shown in FIG. 7. The sponge disks were bonded to the backing layer using a hydraulic press with a heated top platen. Two outer layers (7.6 cm×91.4 cm viscose/polyester spunlace fabric) were placed above and below the backing layer (one outer layer on each side of the backing layer). The fabric layers (top outer layer, backing layer, and bottom outer layer) were then heat sealed together using a bag heat sealer to complete the dressing assembly.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

The invention claimed is:

1. A wound dressing, comprising:
a first outer layer;
a second outer layer; and
a liquid-expandable layer positioned between the first outer layer and the second outer layer, wherein the liquid-expandable layer comprises a plurality of liquid-expandable articles each independently attached to a backing layer,
wherein the backing layer is in sheet form,
wherein the backing layer has a first major surface, and second, opposing major surface and the plurality of liquid-expandable articles is attached to the first major surface and arranged in a predetermined pattern on the backing layer, wherein attachment points of the liquid-expandable articles to the backing layer are substantially coplanar with each other,
wherein the plurality of liquid-expandable articles expand away from the first major surface of the backing layer to form expanded articles upon contact with a liquid,
wherein the expanded articles have a lateral dimension and a longitudinal dimension and expansion of the plurality of liquid-expandable articles is principally along the longitudinal dimension.

2. The wound dressing of claim 1, wherein at least one of the first outer layer and second outer layer comprises a porous material.

3. The wound dressing of claim 1, wherein the first outer layer and second outer layer are joined to form one or more pockets to receive the liquid-expandable layer therein.

4. The wound dressing of claim 1, wherein the plurality of liquid-expandable articles comprises compressed sponge.

5. The wound dressing of claim 4, wherein the compressed sponge comprises regenerated cellulose.

6. The wound dressing of claim 1, wherein the liquid-expandable articles comprise a substantially cylindrical shape.

7. The wound dressing of claim 1, wherein the liquid-expandable articles in the predetermined pattern are spaced sufficiently far apart so that the wound dressing remains flexible.

8. The wound dressing of claim 1, wherein the predetermined pattern defines one or more regions without liquid-expandable articles.

9. The wound dressing of claim 1, wherein the liquid-expandable articles expand to 80% or greater of their maximum expansion capacity within 30 seconds following immersion in water or saline.

10. The wound dressing of claim 9, wherein the volume ratio of expanded articles to liquid-expandable articles is at least 4:1.

11. The wound dressing of claim 1, wherein the first outer layer, the second outer layer and the liquid-expandable layer are laminated to form an elongated sheet.

12. The wound dressing of claim 1, wherein a pre-expansion volume of each liquid-expandable article is from 0.7 mm$^3$ to 7000 mm$^3$.

13. The wound dressing of claim 1, further comprising one or more therapeutic agents coupled to at least one of the first outer layer, the second outer layer and the liquid-expandable layer.

14. The wound dressing of claim 1, further comprising a second plurality of liquid-expandable articles attached to the second major surface.

* * * * *